United States Patent
Tsukada et al.

(10) Patent No.: US 9,610,369 B2
(45) Date of Patent: Apr. 4, 2017

(54) COMPOUND SUITABLE FOR DETECTION OF VESICULAR ACETYLCHOLINE TRANSPORTER

(71) Applicant: HAMAMATSU PHOTONICS K.K., Hamamatsu-shi, Shizuoka (JP)

(72) Inventors: Hideo Tsukada, Hamamatsu (JP); Shingo Nishiyama, Hamamatsu (JP); Takeru Kitashoji, Amagasaki (JP); Tatsuhiro Kobashi, Amagasaki (JP); Yumi Nakamasu, Amagasaki (JP); Hidekazu Nakao, Amagasaki (JP)

(73) Assignees: HAMAMATSU PHOTONICS K.K., Hamamatsu-shi, Shizuoka (JP); NARD INSTITUTE, LTD., Amagasaki-shi, Hyogo, (JP)

( * ) Notice: Subject to any disclaimer, the term of this patent is extended or adjusted under 35 U.S.C. 154(b) by 0 days.

(21) Appl. No.: 14/781,994

(22) PCT Filed: Apr. 2, 2014

(86) PCT No.: PCT/JP2014/059729
§ 371 (c)(1),
(2) Date: Oct. 2, 2015

(87) PCT Pub. No.: WO2014/163106
PCT Pub. Date: Oct. 9, 2014

(65) Prior Publication Data
US 2016/0051711 A1    Feb. 25, 2016

(30) Foreign Application Priority Data
Apr. 5, 2013  (JP) .................................. 2013-079729

(51) Int. Cl.
A61K 51/04       (2006.01)
C07D 295/135     (2006.01)
C07B 59/00       (2006.01)

(52) U.S. Cl.
CPC ........ *A61K 51/0459* (2013.01); *C07B 59/002* (2013.01); *C07D 295/135* (2013.01)

(58) Field of Classification Search
CPC ............ A61K 51/0459; C07D 295/135; C07B 59/002
See application file for complete search history.

(56) References Cited

U.S. PATENT DOCUMENTS 4,018,773 A    4/1977  Condon et al.

FOREIGN PATENT DOCUMENTS

| EP | 1205473 A1 | 5/2002 |
| EP | 1867634 A1 | 12/2007 |
| JP | 11-213321 | * 7/1999 |
| JP | 2012-501344 A | 1/2012 |
| WO | WO-01/07427 A1 | 2/2001 |
| WO | WO-2006/107106 A1 | 10/2006 |
| WO | WO-2010025375 A1 | 3/2010 |

OTHER PUBLICATIONS

JP 11-213321 English Machine Translation (AIPN accessed online May 19, 2016); p. 1-51.*
Greene's Protecting Groups in Organic Synthesis, 2007, Wiley Online Library, Chapter 7; p. 696-926.*
T. Assaad et al., "Synthesis and biodistribution of both (±)-5-[$^{18}$F]-fluoroethoxy and (±)-5-[$^{18}$F]-fluoropropoxy piperazine analogs of benzovesamicol as vesicular acetylcholine transporter ligands (VACht)," Nukleonika, 2013, vol. 58, No. 2, pp. 269-274.
T. Assaad et al., "Radiosynthesis and biological evaluation of $^{123}$I-(±)-trans-2-hydroxy-5-((E)-3-(iodo)allyloxy)-3-(4-phenyl-1-piperazinyl)tetralin," Nukleonika, 2012, vol. 57, No. 1, pp. 81-85.
CN Application No. 201480019776.6—First Office Action issued Jul. 21, 2016 (with machine English translation).
EP Application 14779866.4—Extended European Search Report mailed Sep. 15, 2016.

* cited by examiner

*Primary Examiner* — Samantha Shterengarts
*Assistant Examiner* — Matt Mauro
(74) *Attorney, Agent, or Firm* — Drinker Biddle & Reath LLP (57) ABSTRACT

The present invention provides a compound represented by formula (I), wherein in formula (I), $R^1$ represents $CH_3$, F, $(CH_2)_n$—F, NH—$(CH_2)_n$—F, O—$(CH_2)_n$—F or S—$(CH_2)_n$—F, and n represents an integer of 1 to 3.

[Formula 1]

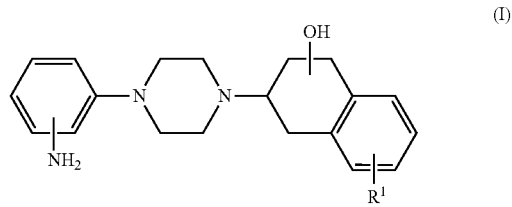

15 Claims, 5 Drawing Sheets

COMPOUND SUITABLE FOR DETECTION OF VESICULAR ACETYLCHOLINE TRANSPORTER

TECHNICAL FIELD

The present invention relates to a compound suitable for detecting a vesicular acetylcholine transporter.

BACKGROUND ART

Alzheimer dementia is a kind of dementia with a deterioration of cognitive function and personality change as main symptoms. Alzheimer dementia is commonly known as Alzheimer's disease.

In patients with Alzheimer's disease, since presynaptic terminals of the cholinergic nervous system have been modified and neural transmission does not sufficiently function, dementia conceivably develops.

In the presynaptic terminals, there are vesicles that store acetylcholine, which is released by nerve stimulation. For taking acetylcholine into the vesicles, vesicular transporters (vesicular acetylcholine transporter) are present on the vesicle membrane. The acetylcholine vesicular transporters are considered to be involved in Alzheimer's disease. If the vesicular acetylcholine transporters can be evaluated, not only diagnosis of Alzheimer's disease but also elucidation of mechanism underlying Alzheimer's disease and development of pharmaceutical products can be realized.

As a compound capable of evaluating the vesicular acetylcholine transporters, for example, a vesamicol piperazine derivative described in Patent Literature 1 is mentioned.

CITATION LIST

Patent Literature

Patent Literature 1: International Publication No. WO 01/07427

SUMMARY OF INVENTION

Problems to be Solved by the Invention

The vesamicol piperazine derivative, however, was designed as a labeling compound available in single photon emission computed tomography (SPECT method). The vesamicol piperazine derivative is unsuitable for positron-emission tomography (PET).

The present invention has been made in view of the above circumstances. An object of the invention is to provide a compound suitable for detecting a vesicular acetylcholine transporter and also available as a labeling compound in the PET.

Means for Solving the Problems

The present invention provides a compound represented by formula (I)

[Formula 1]

(I)

wherein in formula (I), $R^1$ represents $CH_3$, F, $(CH_2)_n$—F, NH—$(CH_2)_n$—F, O—$(CH_2)_n$—F or S—$(CH_2)_n$—F, and n represents an integer of 1 to 3.

A compound represented by formula (I) is a compound suitable for detecting a vesicular acetylcholine transporter.

In formula (I), $R^1$ may be $^{11}CH_3$, $^{18}F$, $(CH_2)_n$—$^{18}F$, N—$(CH_2)_n$—$^{18}F$, O—$(CH_2)_n$—$^{18}F$ or S—$(CH_2)_n$—$^{18}F$, and n represents an integer of 1 to 3. The compound defined in this way can release positrons. The positrons, immediately upon releasing from the compound, bind to electrons and emit γ ray (annihilation radiation). The γ ray is measured by the apparatus used in PET to visualize the body distribution of the compound as an image quantitatively with the passage of time. More specifically, the compound can be used also as a labeling compound in PET.

The compound may be represented by any one of formulas (II) to (V). In formulas (II) to (V), $CH_3$ may be $^{11}CH_3$. The use of these compounds allows efficient measurement by PET.

[Formula 2]

(II)

(III)

(IV)

(V)

The present invention provides a compound represented by formula (VI) or formula (VII)

[Formula 3]

(VI)

wherein in formula (VI), $R^2$ represents an organic group containing B or Sn, OH or SH, and in formula (VII), $R^P$ represents a protecting group of an amino group.

The use of a compound represented by formula (VI) or formula (VII) allows to efficient synthesis of a compound represented by formula (I).

The present invention also provides a vesicular acetylcholine transporter detection reagent containing a compound represented by formula (I). The compound may be a compound represented by either one of formulas (IV) and (V). According to the above vesicular acetylcholine transporter detection reagent, it is possible to efficiently detect a site of a living body at which a vesicular acetylcholine transporter is present.

The present invention provides a diagnostic agent for Alzheimer's disease containing a compound represented by formula (I). The compound may be a compound represented by either one of formulas (IV) and (V). According to the diagnostic agent for Alzheimer's disease, Alzheimer's disease can be diagnosed by efficiently detecting a site of a living body at which a vesicular acetylcholine transporter is present.

The present invention provides a method for detecting a vesicular acetylcholine transporter comprising a step of administering an effective amount of compound represented by formula (I) to a subject. The present invention also provides a method for diagnosing Alzheimer's disease comprising a step of administering an effective amount of compound represented by formula (I) to a subject.

The present invention provides a compound represented by formula (I) for detecting a vesicular acetylcholine transporter. The present invention provides a compound represented by formula (I) for diagnosing Alzheimer's disease.

The present invention provides use of a compound represented by formula (I) for producing a reagent for detecting a vesicular acetylcholine transporter or a diagnostic agent for Alzheimer's disease.

Effect of the Invention

According to the present invention, it is possible to provide a compound suitable for detecting a vesicular acetylcholine transporter, which is also available as a labeling compound in PET.

EMBODIMENTS FOR CARRYING OUT THE INVENTION

Now, preferred embodiments of the present invention will be more specifically described below. However, the present invention is not limited to the following embodiments.

A compound suitable for detecting a vesicular acetylcholine transporter according to the embodiment is a compound represented by formula (I) (hereinafter, sometimes referred to as "Compound (I)").

[Formula 4]

$R^1$ represents $CH_3$, F, $(CH_2)_n$—F, NH—$(CH_2)_n$—F, O—$(CH_2)_n$—F or S—$(CH_2)_n$—F and n represents an integer of 1 to 3. $R^1$ may be $^{11}CH_3$, $^{18}F$, $(CH_2)_n$—$^{18}F$, N—$(CH_2)_n$—$^{18}F$, O—$(CH_2)_n$—$^{18}F$ or S—$(CH_2)_n$—$^{18}F$ (n represents an integer of 1 to 3). If $R^1$ is an organic group containing $^{11}CH_3$ or $^{18}F$, Compound (I) can release positrons. If $R^1$ is $^{11}CH_3$, due to a short half-life of 20 minutes, measurement can be made a plurality of times per day. If $R^1$ is $^{18}F$, $(CH_2)_n$—$^{18}F$, N—$(CH_2)_n$—$^{18}F$, O—$(CH_2)_n$—$^{18}F$ or S—$(CH_2)_n$—$^{18}F$, since the half-life (110 minutes) is longer than in the case of $^{11}CH_3$, it is possible that a single measurement time can be prolonged.

As Compound (I), any one of the compounds represented by formulas (II) to (V) may be used. Hereinafter, compounds represented by formulas (II) to (V) will be sometimes referred to as (S,S) HAPT-A, (R,R) HAPT-A, (S,S) HAPT-B, and (R,R) HAPT-B, respectively. Alternatively, these will be collectively referred to simply as HAPT. In the compounds represented by formulas (II) to (V), $CH_3$ may be $^{11}CH_3$.

[Formula 5]

A compound represented by formula (VI) (hereinafter, sometimes referred to as "Compound (VI)") is a precursor of Compound (I) and preferably used for synthesizing Compound (I) particularly where $R^1$ is $CH_3$.

[Formula 6]

(VI)

$R^2$ is an organic group containing B or Sn, OH or SH. Examples of the organic group containing B or Sn include $-B(OH)_2$, $-Sn(Bu)_3$ and an organic group represented by the following structural formula. An organic group containing B is preferably used for the reason that the organic group generally has low toxicity and rarely put a load to the environment, and that if the organic group is used in combination with a base, the reactivity thereof increases.

[Formula 7]

Compound (VI) may be any one of the compounds represented by formulas (VIII) to (XI).

[Formula 8]

Compound (VI) where $R^2$ is an organic group containing B can be synthesized from a known compound, for example, can be synthesized through synthetic schemes (C) to (F), described in Examples (described later).

Compound (VI) where $R^2$ is an organic group containing Sn can be synthesized from a known compound, for example, through reaction formula (G).

[Formula 9]

(G)

As a method for producing Compound (I) from Compound (VI), any method can be used particularly without limitation as long as it is a known method. For example, Compound (I) where $R^1$ is $^{11}CH_3$ can be synthesized through reaction formula (A).

[Formula 10]

(A)

In reaction formula (A), [¹¹C]CH₃I can be synthesized by a known method, for example, through reaction formula (B).

[Formula 11]

(B)

Compound (I) where $R^1$ is O—$(CH_2)_n$—$^{18}F$ and n is, for example, 2, can be synthesized in accordance with reaction formula (H).

[Formula 12]

(H)

Compound (I) where $R^1$ is $(CH_2)_n$—F and n is, for example, 3, can be synthesized in accordance with reaction formula (I). In the following reaction formula (I), an acetyl group may be de-protected in accordance with a known method such as a method of deprotecting by an acid catalyst.

[Formula 13]

(I)

-continued

A compound represented by formula (VII) (hereinafter, sometimes referred to as "Compound (VII)") is a precursor of Compound (I).

[Formula 14]

(VII)

$R^p$ is not particularly limited as long as it is a protecting group for an amino group and, for example, includes an acetyl group, a tert-butoxycarbonyl group (Boc group) and a 9-fluorenylmethyloxycarbonyl group (Fmoc group).

Compound (VII) can be synthesized, for example, in accordance with synthetic scheme (E) described in Examples (described later).

Compound (I), when it is administered to a living body, tends to specifically bind to a vesicular acetylcholine transporter. Accordingly, if for example, a fluorescent dye or the like, is allowed to bind to Compound (I) or Compound (I) is labeled with a positron, Compound (I) can be used as a labeling compound to a vesicular acetylcholine transporter. In particular, if Compound (I) contains $^{11}CH_3$ or $^{18}F$ as $R^1$, Compound (I) can release positrons. The positrons, immediately upon releasing from Compound (I), bind to electrons and emit γ ray. The γ ray is measured by an apparatus used in PET. In this manner, body distribution of Compound (I) can be visualized as an image quantitatively with the passage of time. In short, if Compound (I) is used, a site of a subject body where a vesicular acetylcholine transporter is present can be detected and its change can be visualized with the passage of time.

Compound (I) is useful as a vesicular acetylcholine transporter detection reagent. The vesicular acetylcholine transporter detection reagent according to the embodiment contains Compound (I). When the reagent is administered to a living body, γ ray is emitted from Compound (I) in the living body. By measuring the γ ray by PET, the site where a vesicular acetylcholine transporter is present can be efficiently detected.

Compound (I) is useful as a diagnostic agent for Alzheimer's disease. According to the diagnostic agent for Alzheimer's disease, the site of a living body where a vesicular acetylcholine transporter is present can be efficiently detected. In this manner, Alzheimer's disease can be diagnosed.

In the vesicular acetylcholine transporter detection reagent and diagnostic agent for Alzheimer's disease according to the embodiment, Compound (I) may be either one of compound represented by formulas (IV) and (V), more specifically, either one of (S,S)HAPT-B and (R,R)HAPT-B. (S,S)HAPT-B and (R,R)HAPT-B are analogous in chemical structure but only (R,R)HAPT-B specifically binds to a vesicular acetylcholine transporter. Therefore, use of (S,S) HAPT-B as a negative control and use of (R,R)HAPT-B as a vesicular acetylcholine transporter labeling compound allow to more accurate detection of a vesicular acetylcholine transporter and diagnosis of Alzheimer's disease. More specifically, the amount of binding, which is obtained by subtracting the amount of (S,S)HAPT-B binding (which is regarded as a non-specific binding) from the amount of binding of (R,R)HAPT-B, is determined as the amount of the specific binding to a vesicular acetylcholine transporter. In this manner, more accurate detection of a vesicular acetylcholine transporter and diagnosis of Alzheimer's disease can be made.

The vesicular acetylcholine transporter detection reagent and diagnostic agent for Alzheimer's disease according to the embodiment can be produced, for example, by dissolving Compound (I) in an arbitrary buffer. In this case, the detection reagent and diagnostic agent are provided as a solution and may contain not only the buffer component but also other components such as a surfactant, a preservative and a stabilizer. As an administration method, usually intravenous administration is employed.

Examples of the target for the vesicular acetylcholine transporter detection reagent and diagnostic agent for Alzheimer's disease according to the embodiment include, but are not limited to, humans, monkeys, mice and rats.

When measurement by PET is performed by using Compound (I) according to the embodiment, the measurement, which is not particularly limited, can be made in accordance with a known method.

EXAMPLES

Now, the present invention will be more specifically described below by way of Examples. However, the present invention is not limited to these examples.

Production Example 1

Synthesis of Compound 6
(N-(2-(piperazin-1-yl)phenyl)acetamide)

Compound 6 was synthesized in accordance with the synthetic scheme of reaction formula (C). Production Examples 1-1 to 1-4 will be more specifically described below.

[Formula 15]

(C)

Production Example 1-1

Synthesis of Compound 12 (tert-butyl-4-(2-nitrophenyl)piperazine-1-carboxylate)

A reaction flask was charged with 2-chloronitrobenzene (168 g, 1.07 mol), Boc-piperazine (199 g, 1.07 mol) and DMSO (1460 ml). To the mixture, potassium carbonate (295 g, 2.13 mol) was further added.

The resultant reaction mixture was allowed to react at 80° C. for 60 hours, poured in ice-cold water (6 L) and extracted with ethyl acetate. The organic layer obtained was washed with water, dried over anhydrous magnesium sulfate, and concentrated under reduced pressure.

The concentrated residue was purified by column chromatography (stationary phase: silica gel, mobile phase: hexane/ethyl acetate=10/1) to obtain Compound 12 (294 g, yield 89.5%).

Production Example 1-2

Synthesis of Compound 13 (tert-butyl-4-(2-aminophenyl)piperazine-1-carboxylate)

A reaction flask was charged with Compound 12 (299 g, 974 mmol) and ethanol. To the mixture, 5% palladium carbon (30 g) was added. The resultant reaction mixture was allowed to react for 2.5 hours while blowing hydrogen gas.

The reaction mixture was filtered and concentrated under reduced pressure to obtain Compound 13 (256 g, yield 94.8%).

Production Example 1-3

Synthesis of Compound 14, (tert-butyl-4-(2-acetamidophenyl)piperazine-1-carboxylate)

A reaction flask was charged with Compound 13 (256 g, 923 mol), methylene chloride (1500 ml) and diisopropylethylamine (179 g, 1.39 mol) and cooled to 0° C. To the resultant reaction mixture, acetyl chloride (87 g, 1.11 mol) was added at 10° C. or less. Thereafter, the reaction mixture was allowed to react at 5 to 10° C. for one hour.

The reaction mixture was poured in a saturated aqueous sodium bicarbonate solution and extracted with methylene chloride. The organic layers were combined, washed with water, dried over anhydrous sodium sulfate and concentrated under reduced pressure.

The concentrated residue was washed with a solvent mixture of ethyl acetate/n-hexane to obtain Compound 14 (275 g, yield 95.2%).

Production Example 1-4

Synthesis of Compound 6,
(N-(2-(piperazin-1-yl)phenyl)acetamide)

A reaction flask was charged with Compound 14 (150 g, 479 mmol) and methylene chloride (1500 ml). To the mixture, trifluoroacetic acid (600 ml, 8.06 mol) was added over 2 hours.

The resultant reaction mixture was allowed to react at ambient temperature for one hour, poured in a saturated aqueous sodium bicarbonate solution and extracted with a solution mixture of chloroform/methanol. The organic layers were combined, washed with water, dried over anhydrous sodium sulfate and purified by column chromatography (NH silica gel, mobile phase: chloroform/methanol=10/1) to obtain Compound 6 (103 g, yield 100%). The $^1$H-NMR measurement results of Compound 6 obtained are shown below.

$^1$H-NMR (300 MHz, CDCl$_3$) δ 8.53 (1H, br s), 8.35 (1H, d), 7.17-7.02 (3H, m), 3.01-3.03 (4H, in), 2.85-2.82 (4H, m), 2.2 (3H, s)

Production Example 2

Synthesis of Compound 24 (2,2,2-trifluoro-N-(1a,2,7,7a-tetrahydronaphtho[2,3-b]oxiren-3-yl)acetamide)

Compound 24 was synthesized in accordance with the synthetic scheme of reaction formula (D). Production Examples 2-1 to 2-3 will be more specifically described below.

[Formula 16]

(D)

Production Example 2-1

Synthesis of Compound 22 (5,8-dihydronaphthalene-1-amine)

Ammonia gas was blown in diethylether (320 ml) at −63° C. to −46° C. until the total volume reached 640 ml, 1-Aminonaphthalene (85.0 g, 594 mmol), 2-methyl-2-propanol (53 ml) and sodium (31.6 g, 1.37 mol) were sequentially added to the above diethylether containing ammonia at −57° C. to −48° C. To the resultant reaction mixture, 2-methyl-2-propanol (53 ml) was further added at −49° C. to −44° C. After the reaction mixture was allowed to react at −52° C. to −44° C. for one hour, the temperature thereof was slowly increased to 25° C. Ethyl alcohol (106 ml) cooled on ice and a saturated aqueous ammonium chloride solution (425 ml) were sequentially added dropwise to the reaction mixture.

The reaction mixture was extracted with ethyl acetate, washed with water and dried over anhydrous sodium sulfate.

The resultant extract solution was concentrated under reduced pressure to obtain Compound 22 (85.1 g, yield 98.7%).

(Production Example 2-2) Synthesis of Compound 23 (N-(5,8-dihydronaphthalen-1-yl-2,2,2-trifluoroacetamide)

A reaction flask was charged with Compound 22 (85.1 g, 586 mmol) and toluene (296 ml). To the mixture, trifluoroacetic anhydride (125 g, 593 mmol) was added dropwise under ice cooling.

The resultant reaction mixture was concentrated under reduced pressure to obtain Compound 23 (142 g, yield 100%).

Production Example 2-3

Synthesis of Compound 24 (2,2,2-trifluoro-N-(1a,2,7,7a-tetrahydronaphth [2,3-b]oxiren-3-yl)acetamide)

A reaction flask was charged with Compound 23 (142 g, 586 mmol) and diethylether (426 ml). To the mixture, m-chloroperbenzoic acid (108 g, 432 mmol) was added under ice cooling.

The resultant reaction mixture was allowed to react at 22° C. to 25° C. for 4 hours. Thereafter, insoluble matter was filtered off from the reaction mixture and the residue was concentrated under reduced pressure.

The concentrated residue was recrystallized from methylene chloride to obtain compound 24 (85.1 g, yield 56%). The $^1$H-NMR measurement results of Compound 24 obtained are shown below,

$^1$H-NMR (300 MHz, DMSO-$d_6$) δ 10.94 (1H, br s), 7.23-7.06 (3H, m), 3.46 (2H, m), 3.23 (2H, m), 3.14-2.87 (2H, m)

Production Example 3

Synthesis of Compound 7-B (N-(2-(4-(5-amino-3-hydroxy-1,2,3,4-tetrahydronaphthalen-2-yl) piperazin-1-yl)phenyl)acetamide)

Compound 7-B was synthesized in accordance with the synthetic scheme of reaction formula (E).

[Formula 17]

(E)

A reaction flask was charged with Compound 6 (55 g, 251 mmol), Compound 24 (71 g, 276 mmol) and ethanol (1150 ml). The reaction was carried out at 78° C. to 79° C. for 16 hours. The resultant reaction mixture was concentrated under reduced pressure and dissolved in methanol (275 ml).

To the reaction mixture, 2N aqueous sodium hydroxide solution (1200 ml) was added. The reaction mixture was stirred for 18 hours and extracted with methylene chloride. The organic layer obtained was dried over anhydrous sodium sulfate and concentrated under reduced pressure.

The concentrated residue was purified by column chromatography (stationary phase: NH silica gel, mobile phase: n-heptane/ethyl acetate=1/2) and recrystallized from ethanol to obtain Compound 7-B (29.6 g, yield 30.0%). The $^1$H-NMR measurement results of the obtained Compound 7-B are shown below.

$^1$H-NMR (300 MHz, CDCl$_3$) δ 8.45 (1H, hr s), 8.36 (1H, d), 7.20-6.98 (4H, m), 6.59-6.55 (2H, m), 4.21 (1H, s), 3.95 (1H, m), 3.64 (2H, s), 3.16 (1H, m), 3.00-2.71 (11H, m), 2.24 (1H, m), 2.24 (3H, m)

Production Example 4

Synthesis of Compound (S,S)-10-B, ((2S,3S)-3-(4-(2-aminophenyl)piperazin-1-yl)-8-(4,4,5,5-tetramethyl-1,3,2-dioxaboran-2-yl)-1,2,3,4-tetrahydronaphthalen-2-ol)

Compound (S,S)-10-B was synthesized in accordance with the synthetic scheme of reaction formula (F). Production Examples 4-1 to 4-3 will be more specifically described below.

[Formula 18]

(F)

7-B (S,S)-8-B (S,S)-9-B (S,S)-10-B

Production Example 4-1

Synthesis of Compound (S,S)-8-B, N-(2-(4-((2S, 3S)-3-hydroxy-5-iodo-1,2,3,4-tetrahydronaphthalen-2-yl)piperazin-1-yl)phenyl)acetamide A reaction flask was charged with Compound 7-B (23.4 g, 61.5 mmol), acetic acid (312 ml) and sulfuric acid (156 ml). To the mixture, an aqueous solution (312 ml) of sodium nitrite (4.86 g, 70.4 mmol) was added dropwise under ice cooling.

The resultant reaction mixture was stirred at −1° C. to 1° C. for 30 minutes and an aqueous solution (156 ml) of potassium iodide (12.6 g, 76.2 mmol) and iodine (9.28 g, 36.6 mmol) were added dropwise to the reaction mixture.

The reaction mixture was allowed to react at 0° C. to 3° C. for 3.5 hours and neutralized with an aqueous sodium hydroxide solution.

The reaction mixture was extracted with a chloroform/methanol mixed solution. The organic layer obtained was dried over anhydrous sodium sulfate and concentrated under reduced pressure.

The concentrated residue was purified by column chromatography (stationary phase: NH silica gel, mobile phase: n-heptane/ethyl acetate=1/2) and the solid matter obtained was washed with methanol to obtain Compound 8-B (2.84 g, yield 9.4%) in the form of racemate. Racemate 8-B was subjected a chiral column (CHIRALPAK IA, mobile phase: chloroform/n-hexane=1/1, flow rate: 10 mL/min) for semi-fractionation and optical resolution was performed. Fractions having a long retention time were collected to obtain Compound (S,S)-8-B (1.18 g, yield 3.9%). Fractions having a short retention time were collected to obtain Compound (R,R)-8-B.

Production Example 4-2

Synthesis of Compound (S,S)-9-B, (2S,3 S)-3-(4-(2-aminophenyl)piperazin-1-yl)-8-iodo-1,2,3,4-tetrahydro naphthalen-2-ol Compound (S,S)-8-B (200 mg, 0.407 mmol) was dissolved in 6N hydrochloric acid (6 mL) and heated to reflux for 2 hours. After completion of the reaction, the reaction solution was cooled to 0° C. in an ice bath and neutralized with a 2N aqueous sodium hydroxide solution. After the reaction solution was extracted with methylene chloride, the organic layer obtained was dried over anhydrous sodium sulfate and concentrated under reduced pressure. The concentrated residue was purified by column chromatography (stationary phase: silica gel, mobile phase: n-heptane/ethyl acetate=4/1 to 3/2) to quantitatively obtain Compound (S,S)-9-B.

Production Example 4-3

Synthesis of Compound (S,S)-10-B, (2S,3 S)-3-(4-(2-aminophenyl)piperazin-1-yl)-8-(4,4,5,5-tetramethyl-1,3,2-dioxaborolan-2-yl)-1,2,3,4-tetrahydronaphthalen-2-ol Compound (S,S)-9-B (170 mg, 0.378 mmol), bis(pinacolato)diboron (96 mg, 0.378 mmol), (dppf) $PdCl_2$/methylene chloride 1/1 complex (77 mg, 0.0945 mmol) and potassium acetate (148 mg, 1.51 mmol) were dissolved in anhydrous dimethyl sulfoxide (10 mL) under an argon atmosphere and heated while stirring at 80° C. for 2 hours. The reaction mixture was cooled to room temperature, poured in water (10 mL) and extracted with ethyl acetate. The organic layer was washed with saturated saline, dried over sodium sulfate and concentrated under reduced pressure. The concentrated residue was purified by column chromatography (stationary phase: NH silica gel, mobile phase: n-heptane/ethyl acetate=7/3). The solid matter obtained was washed well with ethyl acetate and n-heptane ice cooled to obtain Compound (S,S)-10-B (86 mg, yield 50%). $^1$H-NMR measurement results of the obtained Compound (S,S)-10-B are shown below. Note that Compound (R,R)-10-B was obtained from Compound (R,R)-8-B in the same manner as in Production Examples 4-2 and 4-3.

$^1$H-NMR (400 MHz, $CDCl_3$) δ 7.65 (1H, dd, J=1.6, 7.6 Hz), 7.11-7.18 (2H, s), 7.04 (1H, d, J=8.0 Hz), 6.95 (1H, dt, J=1.6, 8.0 Hz), 6.74-6.78 (2H, m), 4.24 (1H, br s), 3.98 (2H, br s), 3.85-3.91 (1H, in), 2.70-3.01 (12H, m), 1.34, 1.33 (12H, s)

Production Example 5

Synthesis and formulation of Compound (R,R)[$^{11}$C]HAPT-B, ((2R,3R)-3-(4-(2-aminophenyl)piperazin-1-yl)-8-[$^{11}$C]methyl-1,2,3,4-tetrahydronaphthalen-2-ol)

(R,R)[$^{11}$C]HAPT-B was synthesized in accordance with the synthetic scheme of reaction formula (A1).

[Formula 19]

(A1)

(R, R)[$^{11}$C]HAPT-B 14N (p,α)$^{11}$C reaction was performed by irradiating nitrogen gas with protons to obtain a positron-emitting radionuclide, i.e., [$^{11}$C] carbon dioxide, (which is carbon dioxide labeled with $^{11}$C). The [$^{11}$C] carbon dioxide was subjected to a reduction reaction with lithium aluminum hydride, a treatment with hydroiodic acid and heating distillation to obtain [$^{11}$C]$CH_3$I.

Tris(dibenzylideneacetone) dipalladium ($Pd_2(dba)_3$) (4.6 mg) and tri-o-tolylphosphine (P(o-Tol)$_3$) (6.2 mg) were dissolved in DMF (0.3 mL) and slightly heated to obtain a solution, the color of which changed from black to slightly yellow. To the resultant solution, [$^{11}$C]$CH_3$I was added.

$K_2CO_3$ (1.4 mg) and Compound (R,R)-10-B (2.0 mg) were dissolved in DMF (0.3 mL). The resultant solution was added to the solution containing [$^{11}$C]$CH_3$I previously obtained.

The reaction mixture was subjected to a methylation reaction performed at 70° C. for 5 minutes. The resultant reaction solution was filtered with a glass filter having a diameter of 13 mm and a pore size of 0.7 μm. The filtrate was introduced in HPLC and separated. A fraction(s) of (R,R)[$^{11}$C]HAPT-B was introduced into an evaporator and then a separation solvent was distilled away by heating under vacuum. To the residue, physiological saline was added to produce a formulation containing a (R,R)[$^{11}$C]HAPT-B.

Production Example 6

Synthesis of Compound 10-Sn, (2R,3R)-3-(4-(2-aminophenyl)piperazin-1-yl)-8-(tributylstannyl)-1,2,3,4-tetrahydronaphthalen-2-ol Compound 10-Sn was synthesized in accordance with the synthetic scheme of the following reaction formula (G1).

[Formula 20]

(G1)

9-B

-continued

10-Sn

A reaction flask was charged with Compound 9-B (265 mg, 0.59 mmol) and toluene (15 mL). The mixture was degassed for 30 minutes while bubbling with argon gas.

Under an argon gas atmosphere, bis(tri-n-butyltin) (635 µL (1.27 mmol)) and tetrakis(triphenylphosphine) palladium (0) (Pd (PPh$_3$)$_4$)(41.1 mg (0.036 mmol)) were added. The reaction mixture was allowed to react at a reflux temperature.

Nineteenth hour, 24th hour, 38th hour from initiation of reflux, tetrakis(triphenylphosphine) palladium (0)(15 mg (0.013 mmol)) and toluene (5 mL) were supplementally added. Twenty second hour from initiation of reflux, bis(tri-n-butyltin)(158 µL (0.32 mmol)) was supplementally added. The reaction mixture was refluxed for 46 hours in total.

The reaction solution was cooled to room temperature, concentrated under vacuum, purified by silica gel column chromatography (silica gel, mobile phase: n-hexane→methylene chloride→methylene chloride/methanol=100/1) to obtain Compound 10-Sn (309 mg, yield 85.5%).

$[\alpha]^{22}$=−22.0 (c=0.138, CHCl$_3$)

Separation purification and verification of synthesis reaction solution

The synthesis reaction solution was separated in the the following HPLC condition.

Column: Megapak SIL C18-10 (JASCO Corporation) (7.6×250 mm)

Solvent: Acetonitrile/30 mM ammonium acetate/acetic acid=450/550/2

Flow rate: 6 ml/min

Detection wavelength: 254 nm

The obtained compound was verified in the following HPLC conditions.

Column: Finepak SIL C18S (JASCO Corporation) (4.6×150 mm)

Solvent: Acetonitrile/30 mM ammonium acetate/acetic acid=500/500/2

Flow rate: 2 ml/min

Detection wavelength: 254 nm

Column: CHIROBIOTIC V (ASTEC) (4.6×250 mm)

Solvent: Methanol/acetic acid/triethylamine=1000/0.3/0.1

Flow rate: 1 ml/min

Detection wavelength: 254 nm (S,S)[$^{11}$C]HAPT-A, (R,R)[$^{11}$C]HAPT-A and (S,S)[$^{11}$C]HAPT-B were produced in the same synthesis route as in Production Example 5. Note that the absolute configuration of HAPT was determined by X-ray analysis.

PET Measurement

Rhesus monkey having a body weight of about 5 kg was immobilized to PET apparatus (trade name, SHR7700 manufactured by Hamamatsu Photonics KK) without anesthesia. After transmission was measured for absorption correction, [$^{11}$C]HAPT was intravenously administered and dynamic measurement was performed for 180 minutes.

Figure 1:
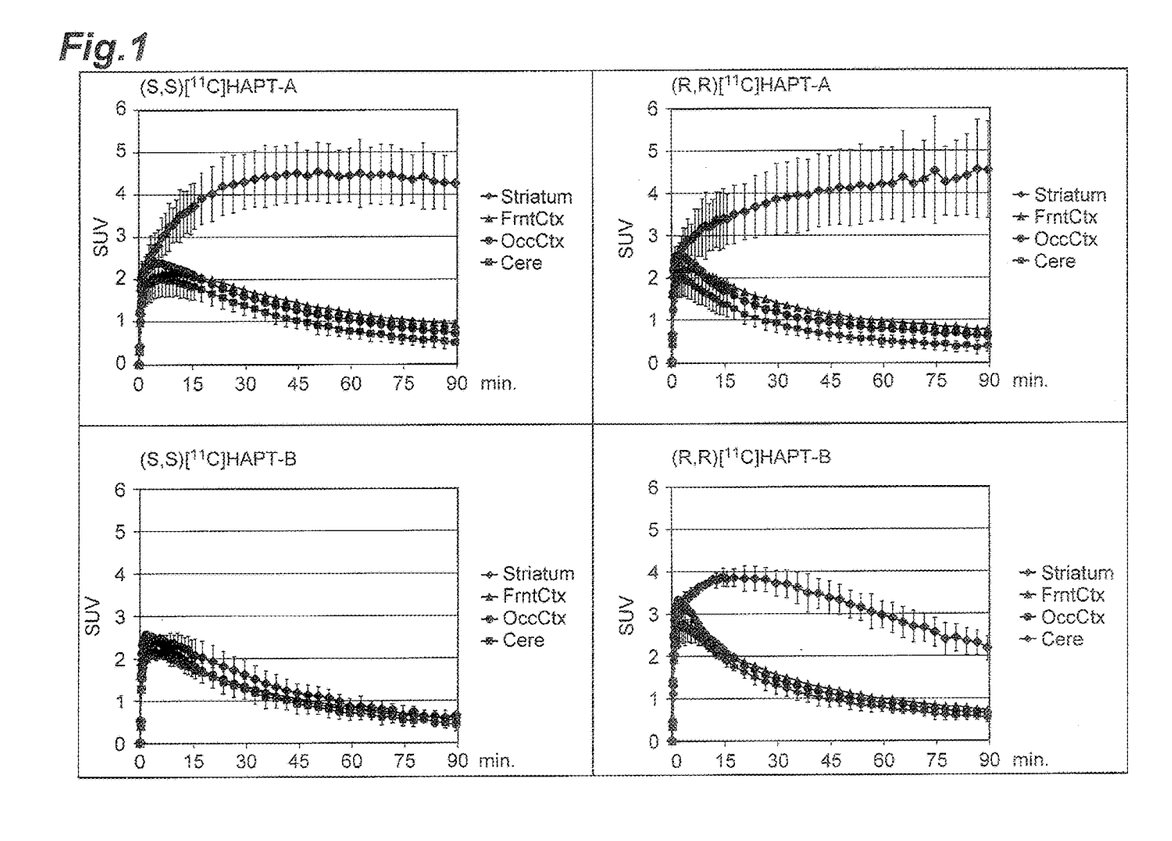
FIG. 1 shows graphs indicating the binding ability of [$^{11}$C]HAPT to vesicular acetylcholine transporters present in the brain of Rhesus monkey (*Macaca mulatta*).

In tomographic images obtained from a single individual by a nuclear magnetic resonance tomography apparatus (hereinafter, MRI), a region of interest (ROI) was determined and then, a time-dependent change of a labeled compound ([$^{11}$C]HAPT) in each ROI was obtained. The results are shown in FIG. 1. It was verified that (S,S)[$^{11}$C]HAPT-A, (R,R)[$^{11}$C]HAPT-A and (R,R)[$^{11}$C]HAPT-B specifically bind to vesicular acetylcholine transporters; whereas (S,S)[$^{11}$C]HAPT-B does not bind to vesicular acetylcholine transporters and binding is non-specific. The results suggested that (S,S)[$^{11}$C]HAPT-B can be used as a negative control, the other three [$^{11}$C]HAPT can be used as a labeling compound to a vesicular acetylcholine transporter. It was suggested that particularly (R,R)[$^{11}$C]HAPT-B, since it reached an equilibrium state in about 15 minutes from initiation of measurement, can be also used in competition experiments.

Figure 2:
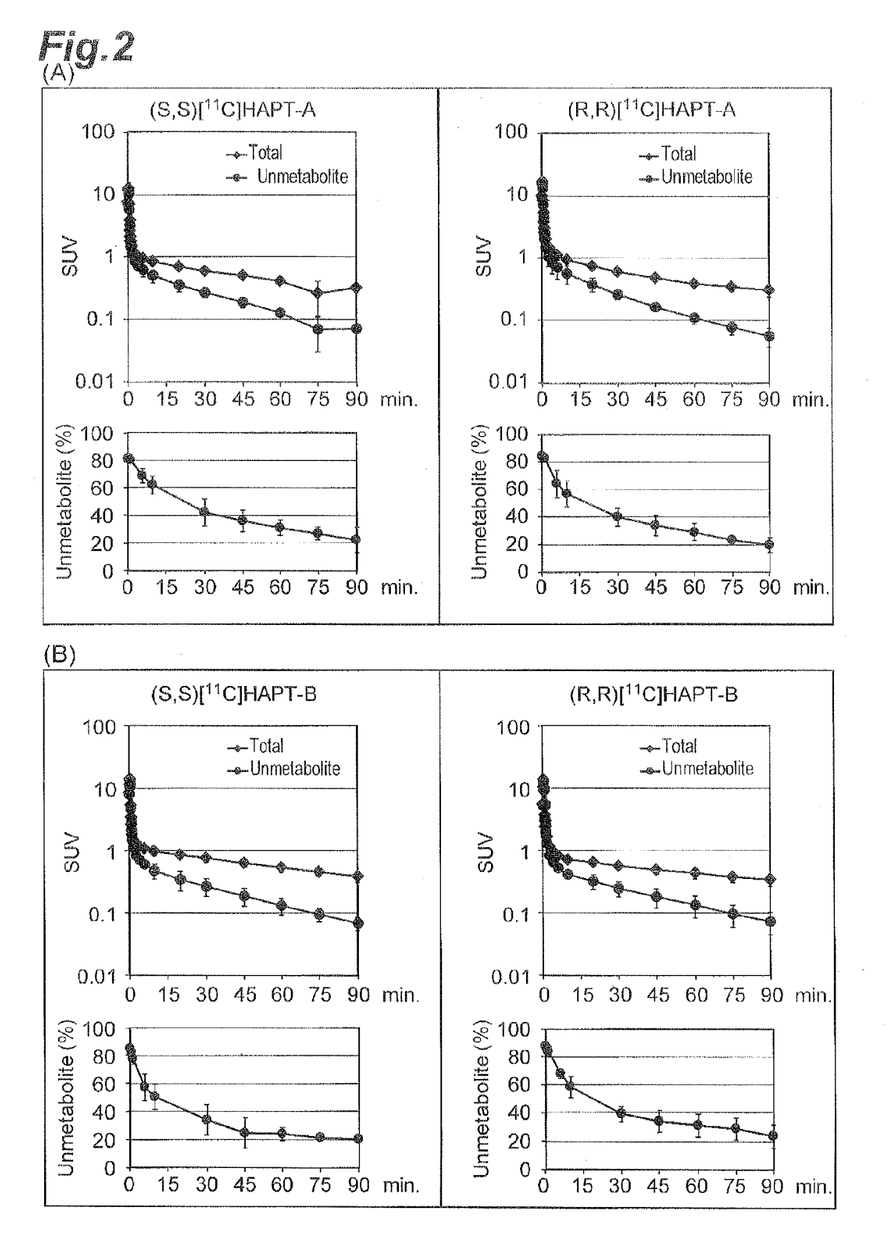
FIG. 2 shows graphs indicating the arterial plasma activity and metabolic activity of [$^{11}$C]HAPT in the brain of Rhesus monkey.

Next, arterial plasma activity and metabolic activity of [$^{11}$C]HAPT were checked. A specific method thereof is as follows. The results are shown in FIG. 2, PET Measurement The cephalic vein or saphenous vein were secured as the route for intravenous administration to test animals and the femoral artery or posterior tibial artery was secured as the route for arterial blood sampling.

A total amount of [$^{11}$C]HAPT was intravenously administered from an indwelling needle placed in a test animal over about 30 seconds. Simultaneously with initiation of administration, Emission measurement (121 minutes, 55 frames in total including: 10 seconds 6 frames, 30 seconds 6 frames, 1 minute 12 frames, 3 minutes 25 frames, 5 minutes 6 frames) was started for monitoring. Note that amount of radioactivity of [$^{11}$C]HAPT actually administrated was obtained through calculation based on the measurement of the radioactivity before administration and the remaining radioactivity in the syringe after administration. In this case, the amount of radioactivity is corrected for half-life based on administration time.

Metabolism Analysis of [$^{11}$C]HAPT

To blood plasma (100 µL) taken from each of the arterial blood samples taken at 16, 40, 64 seconds and 6, 10, 20, 30, 45, 60, 75, 90 minutes after [$^{11}$C]HAPT administration, ethanol (100 µL) was added and stirred. The solution mixture of blood plasma and ethanol was centrifugally separated by a centrifuge at 12000 rpm for 5 minutes to obtain a supernatant. The supernatant obtained was developed on thin-layer chromatography with dichloromethane/diethyl ether/triethylamine=100/40/1 as a solvent. Thereafter, a thin-layer plate on which the supernatant was developed was brought into contact with an imaging plate. Radioactivity distribution on the imaging plate was measured by a fluoro image analyzer to obtain the ratio of a metabolite and unmetabolite.

As a result, it was suggested that there is no fat-soluble metabolite derived from a [$^{11}$C]HAPT and returned to the brain, and found that [$^{11}$C]HAPT is suitable as a labeling compound.

Figure 3:
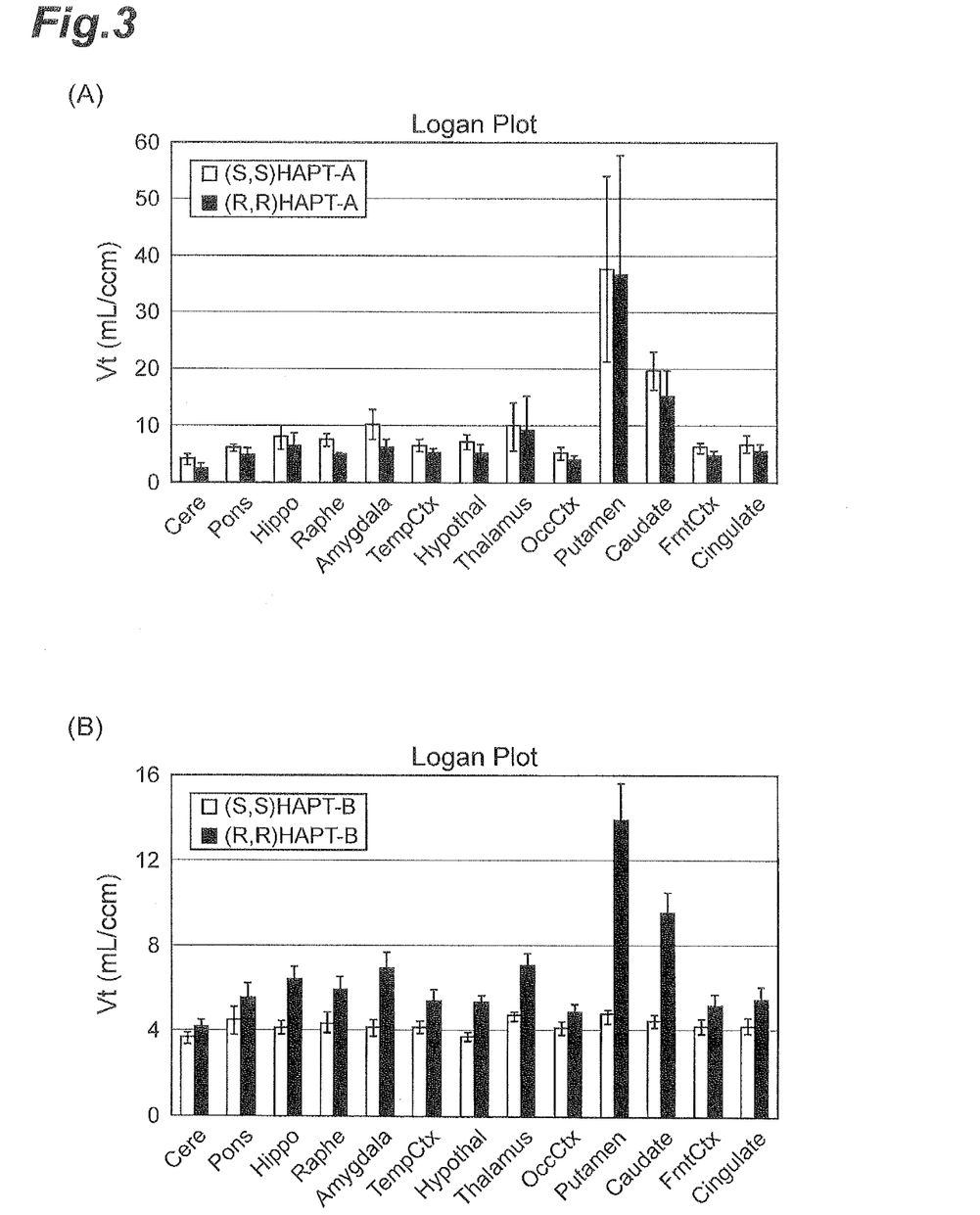
FIG. 3 shows graphs indicating the localization of [$^{11}$C] HAPT in sites of the brain of Rhesus monkey.

Localization of [$^{11}$C]HAPT in individual sites of the brain of Rhesus monkey was checked. The results of the cases of using (S,S)HAPT-A and (R,R)HAPT-A are shown in FIG. 3 (A); whereas the results of the cases of using (S,S)HAPT-B and (R,R)HAPT-B are shown in FIG. 3 (B). As a result of checking the cerebrum, pons, hippocampus, medulla oblongata raphe, amygdala, temporal cortex (TempCtx), hypothalamus, thalamus, occipital cortex (OccCtx), putamen, caudate nucleus, frontal cortex (FmtCtx) and cingulate gyrus, it was found that (S,S)HAPT-A, (R,R)HAPT-A and (R,R)HAPT-B are localized most significantly in the putamen (FIG. 3). In contrast, it was suggested that (S,S) HAPT-B shows non-specific binding in any site.

Figure 4:
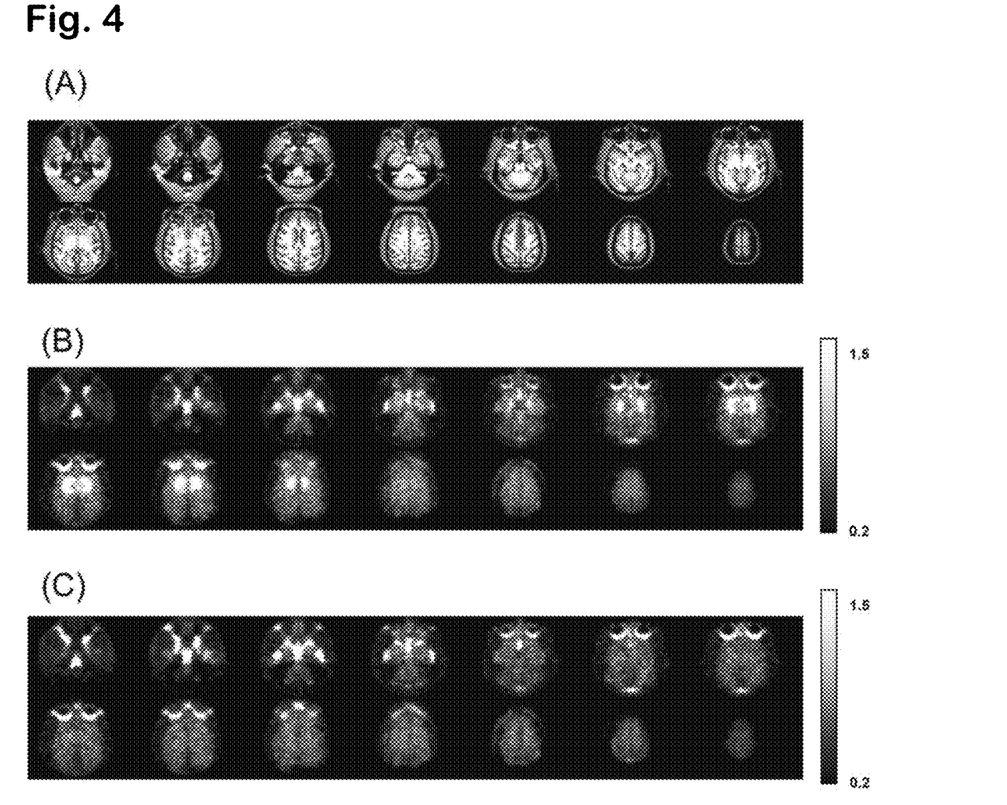
FIG. 4 shows MRI images and PET images of the brain of Rhesus monkey when (R,R)[$^{11}$C]HAPT-B was administered.
Figure 5:
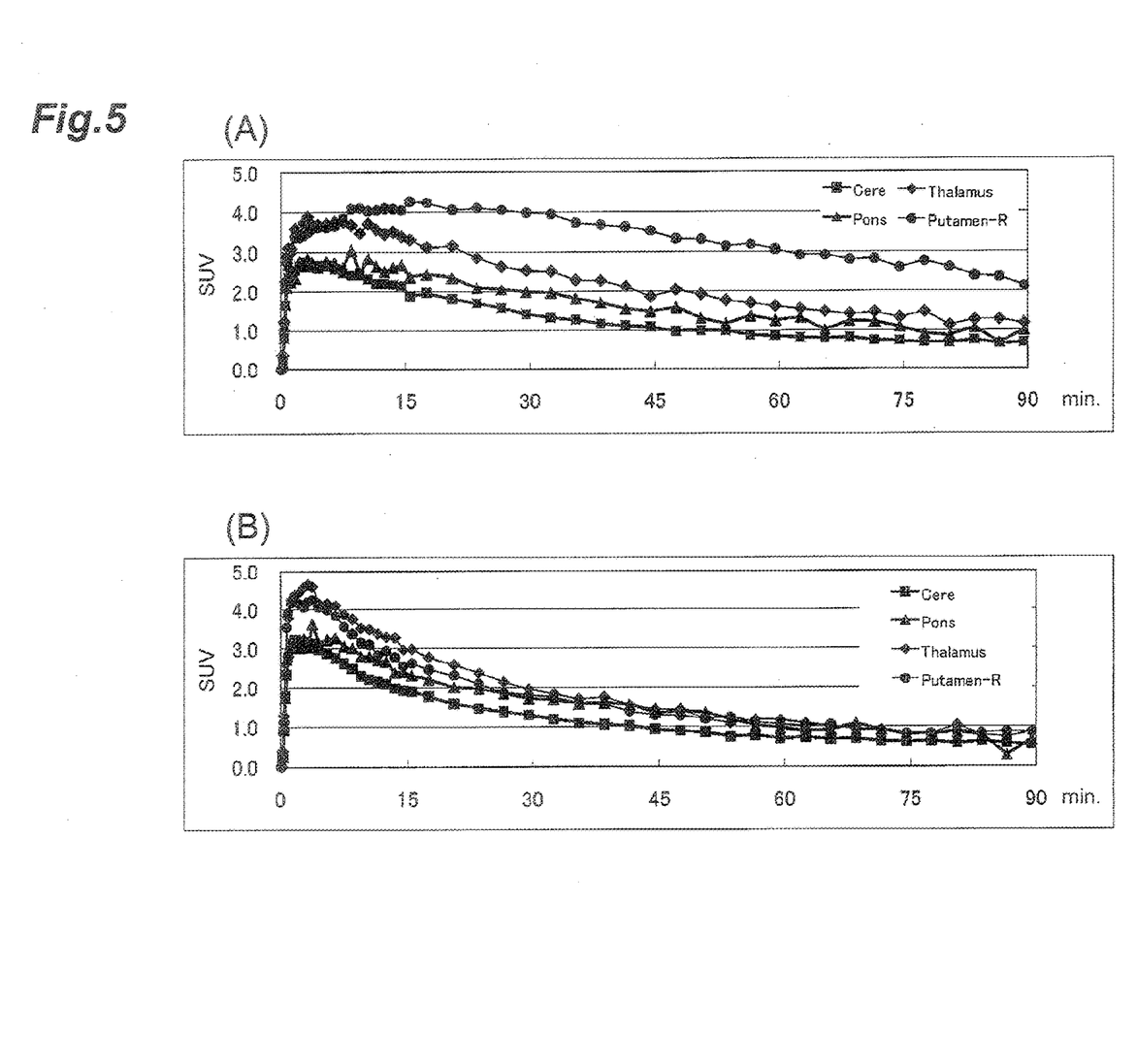
FIG. 5 shows graphs indicating the binding ability of [$^{11}$C]HAPT in sites of the brain of Rhesus monkey when [$^{11}$C]HAPT was competitively administered with vesamicol.

Inhibition experiments were performed by using a vesicular transporter inhibitor (vesamicol). Specific procedure employed is as follows. The results are shown in FIGS. 4 and 5.

PET Measurement

The cephalic vein or saphenous vein was secured as the route for intravenous administration to test animals and the femoral artery or posterior tibial artery was secured as the route for arterial blood sampling.

Thirty minutes before administration of [$^{11}$C]HAPT, L-(−)-vesamicol was intravenously administered in a dose of 1 mg/kg.

The amount of radioactivity of [$^{11}$C]HAPT before administration was measured. A total amount of [$^{11}$C]HAPT was intravenously administered from an indwelling needle placed in a test animal over about 30 seconds. Simultaneously with initiation of administration, Emission measurement (121 minutes, 55 frames in total including: 10 seconds 6 frames, 30 seconds 6 frames, 1 minute 12 frames, 3 minutes 25 frames, 5 minutes 6 frames) was started for monitoring.

It was found that in the experiments where vesamicol was administered (FIG. 4 (C), FIG. 5 (B)), compared to control experiments (FIG. 4 (B), FIG. 5 (A)) where vesamicol was not administered, binding of (R,R)[$^{11}$C]HAPT-B to vesicular acetylcholine transporters reduces. As a result, it was suggested that (R,R)[$^{11}$C]HAPT-B is suitable for competition experiments.

The invention claimed is:

1. A compound represented by formula (I):

wherein in formula (I), R$^1$ represents CH$_3$, F, (CH$_2$)$_n$—F, NH—(CH$_2$)$_n$—F, O—(CH$_2$)$_n$—F or S—(CH$_2$)$_n$—F, and n represents an integer of 1 to 3.

2. The compound according to claim 1, wherein R$^1$ is $^{11}$CH$_3$, $^{18}$F, (CH$_2$)$_n$—$^{18}$F, —(CH$_2$)$_n$—$^{18}$F, O—(CH$_2$)$_n$—$^{18}$F or S—(CH$_2$)$_n$—$^{18}$F, and n represents an integer of 1 to 3.

3. The compound according to claim 1, represented by any one of formulas (II) to (V):

4. The compound according to claim 3, wherein CH$_3$ is $^{11}$CH$_3$.

5. A compound represented by formula (VI):

wherein in formula (VI), R$^2$ represents OH, SH, or an organic group containing B.

6. A vesicular acetylcholine transporter detection reagent, containing a compound according to claim 1.

7. A diagnostic agent for Alzheimer's disease, containing a compound according to claim 1.

8. The vesicular acetylcholine transporter detection reagent according to claim 6, wherein the compound is a compound represented by either one of formulas (IV) and (V):

-continued (V)

9. The diagnostic agent for Alzheimer's disease according to claim 7, wherein the compound is a compound represented by either one of formulas (IV) and (V):

(IV)

-continued (V)

10. A vesicular acetylcholine transporter detection reagent, containing a compound according to claim 2.

11. A vesicular acetylcholine transporter detection reagent, containing a compound according to claim 3.

12. A vesicular acetylcholine transporter detection reagent, containing a compound according to claim 4.

13. A diagnostic agent for Alzheimer's disease, containing a compound according to claim 2.

14. A diagnostic agent for Alzheimer's disease, containing a compound according to claim 3.

15. A diagnostic agent for Alzheimer's disease, containing a compound according to claim 4.

* * * * *